United States Patent [19]
Eckles

[11] 4,312,218
[45] Jan. 26, 1982

[54] POROMETER AND METHOD FOR STOMATAL MEASUREMENTS

[75] Inventor: Robert D. Eckles, Lincoln, Nebr.

[73] Assignee: Li-Cor, Inc., Lincoln, Nebr.

[21] Appl. No.: 71,847

[22] Filed: Sep. 4, 1979

[51] Int. Cl.³ .................... G01N 33/00; G01N 33/48
[52] U.S. Cl. .................................. 73/76; 73/432 R; 364/557
[58] Field of Search .............. 73/76, 861.85, 1 G, 73/38, 198; 364/557, 413

[56] References Cited

U.S. PATENT DOCUMENTS

| | | | |
|---|---|---|---|
| 3,208,275 | 9/1965 | Thornthwaite et al. | 73/861.85 |
| 3,463,000 | 8/1969 | Broadwin | 73/76 |
| 3,557,617 | 1/1971 | Wilson et al. | 73/861.85 |
| 3,688,309 | 8/1972 | Volberg | 73/73 X |
| 3,894,419 | 7/1975 | Mator et al. | 73/1 G |
| 3,909,598 | 9/1975 | Collins | 73/76 X |
| 3,973,431 | 8/1976 | Ginhou | 73/76 |
| 4,009,614 | 3/1977 | Sheppard et al. | 73/198 X |
| 4,044,238 | 8/1977 | Emschermann et al. | 364/557 X |
| 4,160,374 | 7/1979 | Crump et al. | 73/76 |

FOREIGN PATENT DOCUMENTS

470281 8/1975 U.S.S.R. .............................. 47/58

*Primary Examiner*—Daniel M. Yasich
*Attorney, Agent, or Firm*—Vincent L. Carney

[57] ABSTRACT

To measure stomatal resistance of a leaf, signals are obtained from: (1) a small thermocouple positioned adjacent to the leaf in a cuvette to measure temperature of the leaf without conducting excessive heat; (2) a thermistor in the cuvette chamber; and (3) a moisture sensor in the chamber. The moisture signal automatically controls a magnetically operated bypass valve from a source of air flowing through the cuvette chamber so that the moisture remains constant while the flow rate of the air is varied. The flow rate is measured in a flow meter having two laminar paths in series, composed of equal-length equal-diameter tubes but differing in the number of tubes, with the flow rate being measured in a different one of two tubes in each path for different scale measurements.

46 Claims, 6 Drawing Figures

POROMETER AND METHOD FOR STOMATAL MEASUREMENTS

GENERAL FIELD OF THE INVENTION, ITS BACKGROUND AND PRIOR ART

This invention relates to porometers and methods of stomatal measurement.

In one class of porometer, called a steady-state diffusion porometer, the moisture in a cuvette is measured and a dry gas is forced through the cuvette to maintain the moisture constant. A leaf in the cuvette has its transpiration and diffusion resistance measured by measuring the flow of air and the water vapor density of water in the chamber, using known formulae. Water vapor density is determined from temperature and moisture.

It has also been proposed to use a more refined formula for diffusion resistance in which the water vapor density within the leaf and the water vapor density in the chamber are both measured.

In the prior art instruments of this class, the rate of flow of the dry gas is manually adjusted and a meter measures the rate of flow. This instrument has a disadvantage in that it only measures the temperature and moisture in the chamber and does not measure the temperature of the leaf so that it is in error in certain ranges. Moreover, it cannot adjust instantaneously to changes of vapor pressure so that its calculations are in error at times because of sudden changes in the leaf.

Accordingly, it is an object of the invention to provide a novel porometer.

It is a further object of the invention to provide a novel method for measuring stomatal characteristics of plants.

It is a still further object of the invention to provide a novel flow meter for use in porometers.

It is a still further object of the invention to provide a novel technique and equipment for controlling the flow of air through a porometer.

It is a still further object of the invention to provide a precise technique for measuring the temperature of a leaf in a porometer.

SUMMARY OF THE INVENTION

In accordance with the above and further objects of the invention, a portion of a plant, characteristics of which are to be measured, is mounted with a part of its surface in a cuvette. A leaf is the usual part of the plant. While the leaf is in the cuvette, a dry gas is forced through the cuvette to maintain the moisture in the cuvette constant, with the rate of flow of gas being automatically controlled by a moisture sensor in the cuvette. The moisture sensor controls a bypass valve from the source of gas. Vapor density is measured in the cuvette at first times and the diffusion resistance and transpiration rate of the leaf are calculated at second times based on the measurements at the first times and are thus independent of the vapor density at the second times.

To increase the accuracy of the measurement of the diffusion resistance, the temperature of the leaf is measured with a very small thermocouple and the vapor density of water in the leaf is calculated as well as the vapor density in the cuvette from the temperature and moisture in the cuvette.

For further precision, the flow meter causes the dry gas to flow through first and second paths in series, both of which are entirely laminar and measures flow rate in both paths. The gas flows through a single narrow first tube in one path with laminar flow and flow rate is measured through that tube to provide a precise measurement when the flow rate is low. In the other path, the gas flows through parallel second tubes, each of which is equal in length and diameter to the first tube. One of the second tubes in the parallel path has the flow rate measured through it to provide a precise measurement for higher rates of flow, when multiplied by the number of parallel second tubes.

SUMMARY OF THE DRAWINGS

The above noted and other features of the invention will be better understood from the following detailed description when considered in connection with the accompanying drawings in which.

GENERAL STRUCTURE

Figure 1:
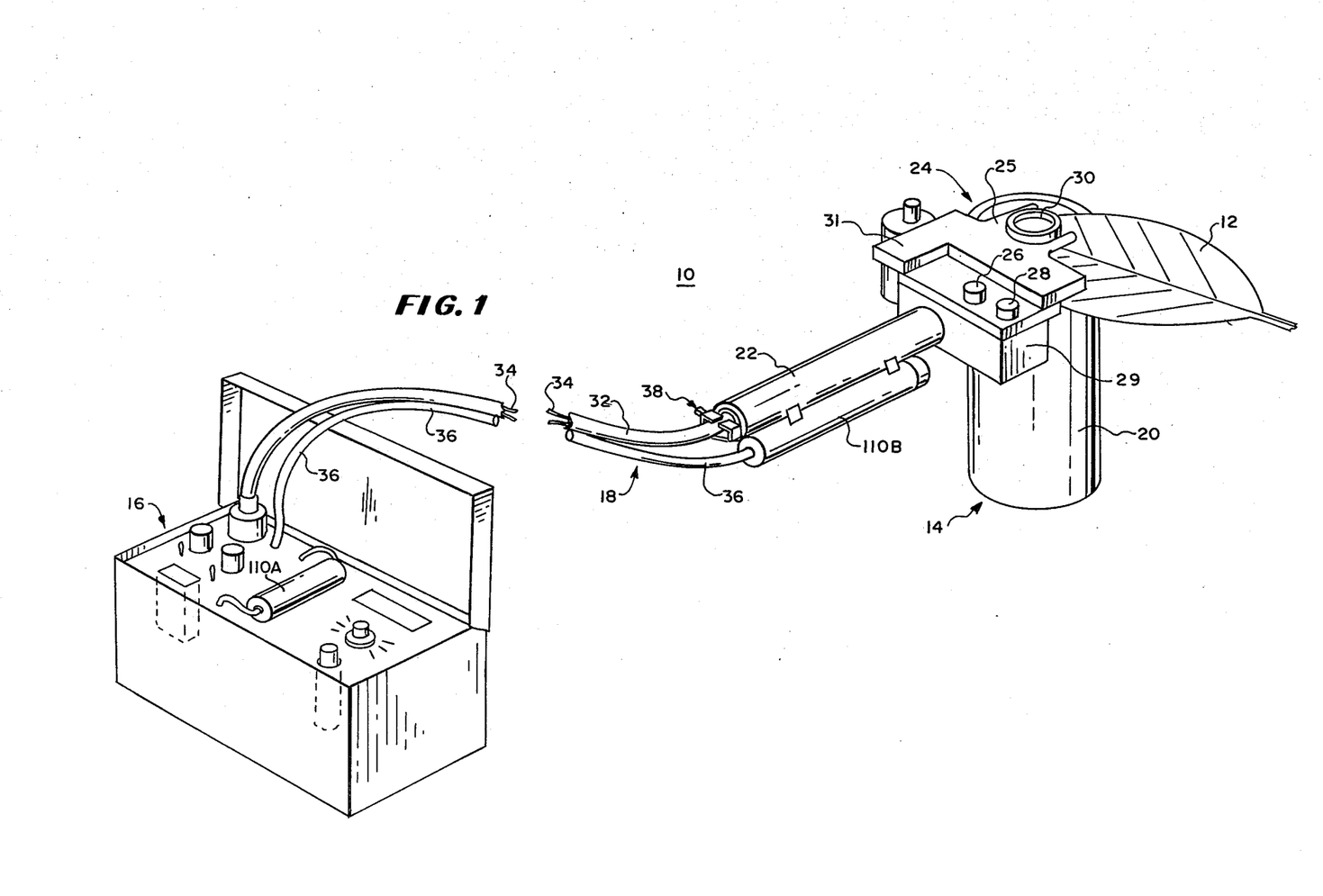
FIG. 1 is a fragmentary, simplified, perspective view of a porometer in accordance with an embodiment of the invention.

In FIG. 1, there is shown a steady-state diffusive resistance meter 10 used to measure the diffusive resistance of plants or parts of plants such as the leaf shown at 12 and having as its principal parts a cuvette 14 and a console unit 16 connected together by a cable 18.

The cuvette 14 includes an outer cylindrical sheath 20, a handle 22, and a lever 24, with the lever 24 being pivotally mounted to the outer sheath 20 and the handle 22 extending orthogonally to the central axis of the cylindrical sheath 20.

To provide for electrical and pneumatic connection between the console unit 16 and the cuvette, the handle 22 is a cylindrical tube adapted to receive within it the cable 18 and includes a cable stretcher to apply tension to the cable. Thus the handle serves an additional function of providing a convenient mechanism for extending the cable through and into the sheath 20 where the cable conductors and conduit to be described hereinafter are connected to apparatus within the cuvette 14.

The lever 24 is pivotally mounted to the sheath 20 and includes a semicircular upper flat surface 25 with a cutaway portion forming an extending finger 31 parallel to the handle 22 for pivoting the lever 24 to lift one end of the flat surface 25. The cutaway portion exposes a switch compartment 29 from which two actuator arms 26 and 28 of first and second switches respectively extend. A cylindrical opening 30 extends through the flat surface 25 of the lever 24 to form an open upper part of a cylindrical compartment which holds the leaf 12 between the flat surface 25 and the sheath 20.

The cable 18 includes an outer sheath 32, fifteen electrical conductors indicated generally at 34 and an attached air conduit 36 which communicates at one end with a pump within the console 16 and at the other end with an inner chamber within the cuvette 14. The cable 18 is grasped by a cable stretcher, one end of which is shown at 38 to provide tension and protect it in a manner known in the art from being pulled free of the cuvette 14.

GENERAL OPERATION

Broadly, the stead-state diffusive resistance porometer 10 calculates the diffusive resistance and the transpiration of a leaf such as that shown at 12. This calculation is performed with information it first obtains by: (1) measuring the temperature at the surface of the leaf; (2) measuring the temperature of a chamber communicating with the leaf: (3) measuring the humidity of the chamber; and (4) rate of flow of air through the chamber.

To measure the temperature of the leaf 12 and the temperature of the chamber communicating with the leaf, the arm 31 is depressed to raise the distal portion of the lever 24 which portion includes the flat surface 25. A portion of the leaf is inserted between the flat portion 25 and the outer sheath 20. The lever 24 is then released and the leaf is held downwardly against a cuvette chamber.

As the leaf is pressed downwardly by the lever 24, it presses against a small thermocouple (not shown in FIG. 1) which measures the temperature of its surface. The thermocouple is sufficiently small so that it is precise and not affected substantially by heat conductivity through the metal of the thermocouple. At the same time the temperature and humidity within the chamber are measured by a thermistor and a capacitive sensor in the chamber while the air in the chamber is circulated by an internal fan.

To calculate the diffusive resistance and the transpiration of the leaf, dry air is moved through the chamber at a rate which maintains the measured humidity constant and the diffusive resistance and transpiration are calculated from the rate of flow of the dry air, the area of the leaf within the opening 30 and the temperatures of the leaf and chamber. The temperatures are used to obtain the vapor densities from known tables One such set of tables is shown on pages 1358-1360 of "LANGE'S HANDBOOK OF CHEMISTRY" compiled and edited by Norbert Adolph Lange and published by Handbook Publishers, Inc., Sandusky, Ohio, 1946. In the preferred embodiment, data from Smithsonian Meterological Tables were used. That data was published in Bulletin 809 of the College of Agriculture Research Center, Washington State University, Pullman, Wash. 99163, dated June 1975.

The diffusive resistance is calculated from equation 1 and the transpiration is calculated from equation 2 where R equals the diffusive resistance, $C_e$ equals the saturation vapor density at the surface of the leaf, $C_a$ equals the vapor density of the air in the chamber, A equals the area of the leaf, F equals the rate of flow of air in cubic centimeters per second and T equals transpiration.

EQUATIONS 1 AND 2

$R = (C_e/C_a - 1) A/F$       EQUATION 1:

$T = F C_a/A$       EQUATION 2:

To maintain the humidity constant within the chamber by controlling the rate of flow of air, the conduit 36 communicates with a bypass valve located between the source of air and cuvette (not shown in FIG. 1) controlled by the humidity sensor and a flow rate measuring device. The bypass valve alters the rate of flow of air through the conduit 36 into the chamber to maintain the humidity constant.

To measure the flow rate, a plurality of small diameter tubes in the air path create a laminar flow which is measured across the wide dynamic range as will be described hereinafter. The signal from this measurement is compared to the humidity signal at a set value and an error signal from the comparison controls the bypass valve automatically as will be explained hereinafter in greater detail. The push-button switches 26 and 28 permit a set reading of diffusive resistance to be maintained in memory to be erased later as will be explained hereinafter.

COMPONENTS

Figure 2:
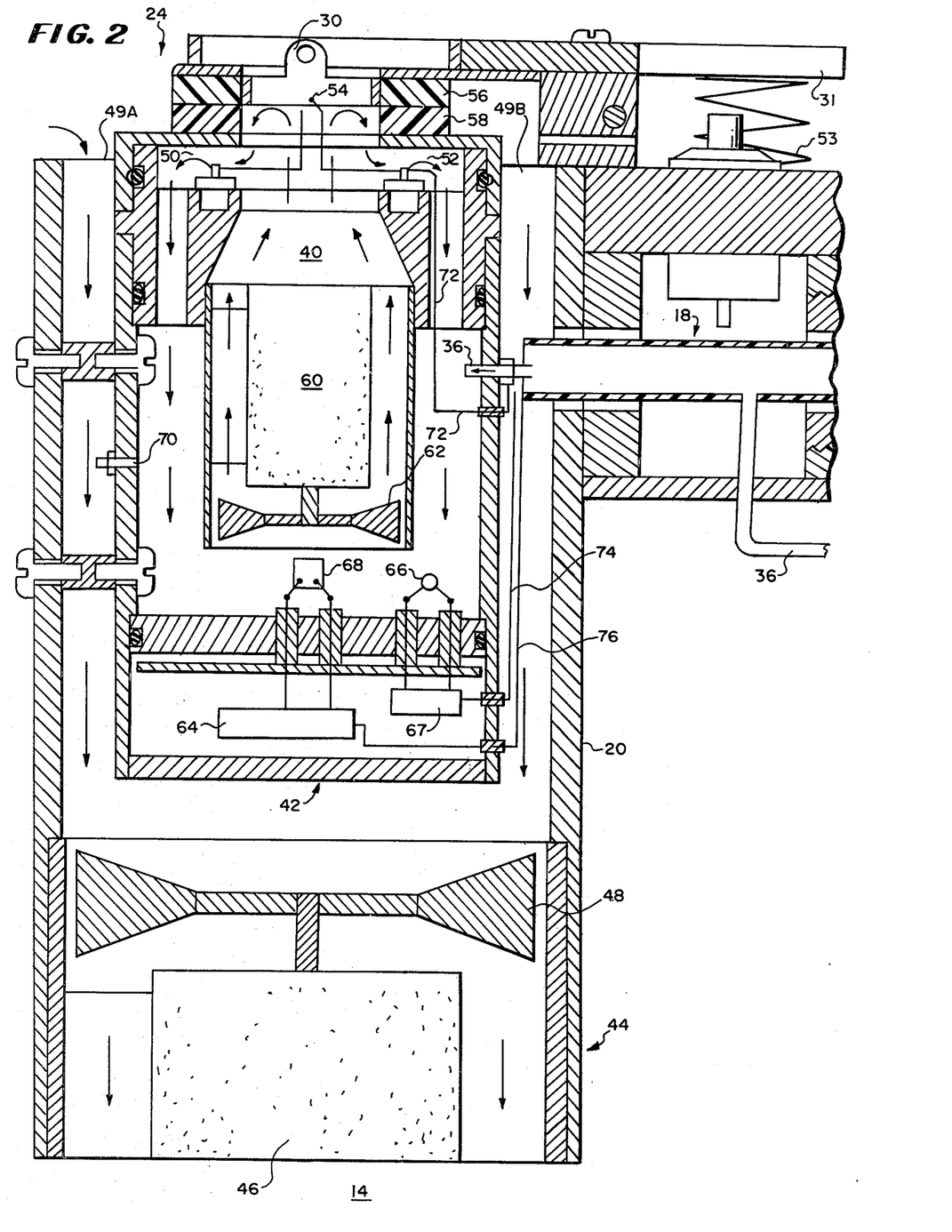
FIG. 2 is a simplified, sectional, fragmentary elevational view of a portion of the embodiment of FIG. 1.

In FIG. 2, there is shown a simplified, sectional, fragmentary elevational view of the cuvette 14 having an inner cuvette chamber 40, an amplifier section 42, and a shroud cooling section 44.

To cool the external housing and circuitry, the cooling compartment 44 includes a motor 46 attached by a shaft to a fan 48 which provides the flow of air over the amplifier section 42 and the inner cuvette chamber 40. The fan 48 draws air downwardly through a plurality of tubular cylinders circumferentially spaced around the compartments 40 and 42, two of which are shown at 49A and 49B, and exhausts it out of the bottom of the shroud as shown by the arrow.

To measure the temperatures of the leaf, the inner cuvette chamber 40 includes first and second conductive posts 50 and 52 positioned close to the lever 24 and directly under the aperture 30 (FIG. 1). Between these two posts, a small thermocouple 54 is mounted and biased upwardly. The thermocouple 54 is sufficiently small so that the conductivity of heat through it is negligible when compared to the conductivity of the leaf. In the preferred embodiment, the thermocouple 54 is one mil in diameter.

To press the leaf against the thermocouple 54, a first O-ring 56 is mounted to the underside of the lever 24 around the opening 30 and a second O-ring 58 is mounted to the top of the chamber 40 around the edge of an opening thereto and aligned with O-ring 56. The lever 24 is biased closed by a compression spring 53 so that the leaf, when inserted as shown in FIG. 1, is pressed downwardly with an area of its top equal to the opening 30 being exposed to air and a corresponding part of its bottom communicating with the top part of the compartment 40 for measurement of the diffusive resistance and its transpiration.

The wire thermocouple 54 has a portion extending upwardly into a position just above the O-ring 58 and centered in its open center. Thus, it extends to the midpoint between O-rings 56 and 58 so that the O-rings define between them an opening for holding the leaf 12 (shown in FIG. 1) in contact with the thermocouple. With this construction, the leaf contacts a small part of the thermocouple against its surface between the O-rings to define an area between the O-rings 56 and 58 with the top part of the leaf being exposed to the atmosphere and a small part of the bottom being connected to the thermocouple 54.

To circulate air within the cuvette chamber 40, a fan motor 60 is mounted and drives a fan 62 to impel air upwardly against the leaf. The air circulates radially across the top of the cuvette chamber 40 and downwardly around the sides of the compartment to the bottom to provide continuous symmetrical circulation of the air upward into the leaf within the opening 30 and then down again across the walls of the chamber to recirculate back to the fan. The air conduit 36 extends through the wall and into the chamber 40 and there is an exhaust port 70 through the wall of the chamber 40 to permit dry air to flow through the chamber 40.

Mounted near the bottom of the chamber 40 in the path of circulation by the fan is a thermistor 66 for measuring the temperature in the chamber and a moisture sensing capacitor 68 for measuring the moisture in the chamber. The thermistor 66 and the moisture sensing capacitor 68 are electrically connected to circuitry shown at 67 and 69 within the amplifier section 42, with the thermistor being electrically connected to amplifiers therein and the moisture sensing capacitor 68 being connected to a source of oscillations, the amplitudes of which are changed in proportion to the moisture within the chamber. This circuitry is conventional and will not be described further.

The conductors from the sensors are electrically connected to the cable 18 as illustrated schematically. The conductors providing electrical connection to the thermocouple 54, the thermistor 66 and the moisture sensing capacitor 68 are indicated schematically at 72, 74 and 76 respectively. The thermistor 66 is shown connected to amplifying circuitry and the moisture sensing capacitor 68 is shown connected to the pulse generator and amplifying equipment. Both units include conventional calibration arrangements so that factory adjustment of the values read from them may be made to provide sufficiently precise output signals indicating temperature and moisture.

Figure 3:
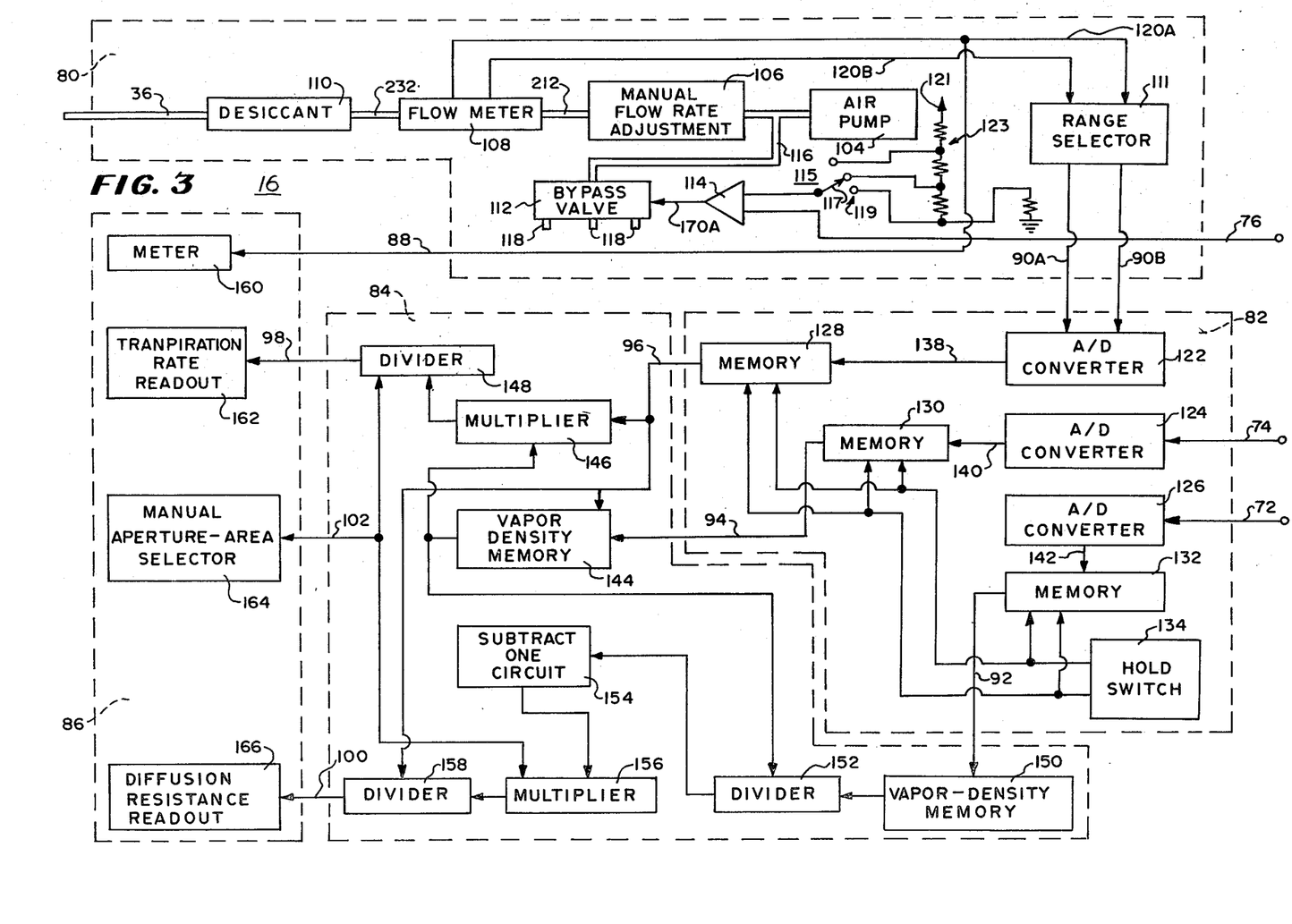
FIG. 3 is a block diagram illustrating the operation of the embodiment of FIG. 1.

In FIG. 3, there is shown a block diagram of the console 16 indicating generally the functions performed by circuitry within the console. In the preferred embodiment, the functions shown by the blocks are performed by a microprocessor programmed in the conventional way for such operations. An RCA 1802, CDP 1802 COSMAC microprocessor has been used, programmed in accordance with the established procedures for that microprocessor.

Full information about that microprocessor is available in the "User Manual for the CDP 1802 COSMAC Microprocessor" from RCA Corporation, Solid State Division, Somerville, N.J. 08876. This information is incorporated by reference.

As shown in FIG. 3, the console 16 includes the air flow section 80, a data conversion section 82, a calculator section 84, and a display and leaf-size selection section 86.

The air flow section 80 is connected to the cuvette 14 to provide the dry air flow through the conduit 36 to the cuvette 14 (FIG. 1) and to receive a signal on conductor 76 indicating the moisture. It is connected to the display and leaf-size selection section 86 to provide signals on a conductor 88 and to the data conversion section 82 to provide signals through a conductor 90 indicating the flow rate of air in conduit 36 through the cuvette 14 (FIG. 1).

The data conversion section 82 is connected to the cuvette 14 (FIG. 1) to receive signals indicating the leaf temperature through conductor 72 and the chamber temperature through a conductor 76 and converts that data to discrete periodic digital form for application to the calculation section 84 through conductors 92, 94 and 96 together with flow rate data received on conductors 90 and 92 from the air flow section 80.

The calculator section 84 is electrically connected to the display and leaf-size selection section 86 by conductors 98 and 100 to indicate the transpiration rate and the diffusion resistance and through a conductor 102 to receive information concerning the selected leaf size, which is controlled by the type of lever 24 in the cuvette 14 (FIG. 2).

To provide a flow of dry air to the conduit 36, the air flow section 80 includes an air pump 104, a manual flow rate adjustment 106, a flow meter 108, and a desiccant 110, with the manual flow rate adjustment 106, the flow meter 108 and the desiccant 110 being connected in series in the order named between the pump 104 and the conduit 36 leading to the cuvette 14 (FIG. 1).

The manual flow rate adjustment 106 is a manually controlled valve to provide an approximate control of the rate of flow of air in the conduit 36.

To control the rate of flow of air over a wide dynamic range as the moisture within the cuvette 14 changes, the air flow section 80 includes a bypass valve 112, a differential amplifier 114, a range selector 111 and a selector switch 115, with the bypass valve 112 communicating with the conduit between the manual flow adjustment and the pump 104 through a conduit 116.

The bypass valve 112 automatically controls the flow of air between the conduit 116 and exhaust port 118 to reduce the flow rate into the conduit 36 from the pump 104 by permitting air to escape at a controlled rate. The differential amplifier 114 controls the bypass valve 112 in accordance with a signal received from the moisture sensing capacitor 68 (FIG. 2) in the cuvette 14 through a conductor 76 indicating the moisture in the cuvette. The signal on conductor 76 is compared by the differential amplifier by a signal provided to it by the selector switch 115.

The selector switch 115 includes a switch arm or armature 117, a plurality of stationary contacts indicated generally at 119, a source of DC power 121, and a plurality of resistances connected in series indicated generally at 123. Stationary contacts 119 are each electrically connected to a different point within the series of resistances 123 between the source of power 121 and ground so as to each have a different potential. One of the contacts is open.

To develop a signal which maintains the humidity in the cuvette constant, the armature 117 is electrically connected to one of the inputs of the differential amplifier 114 so that as it is moved from position to position, a different potential may be applied to the reference inputs of the differential amplifier 114 to establish a null point which is automatically maintained by the bypass valve 112. The bypass valve, in response to a signal from the differential amplifier indicating a change in humidity, adjusts the flow of dry air into the inner cuvette to maintain the moisture as indicated by the signal on conductor 76 at a level corresponding to the position of the switch 117.

In the preferred embodiment as described in connection with FIG. 6, the humidity is measured and stored in memory at a time selected by depressing push-button 26. This stored value establishes the null point.

During the operation of the air flow section 80, air is pumped at a steady rate from the pump 104 into the manual flow rate adjustment 106. The adjustment is set from the front of the panel by the operator to approximately the value the operator wishes.

The air flows through the flow meter 108 and is indicated in terms of flow rate on the display and leaf-size selection section 86. It flows through a desiccant 110 such as silica gell and from there into the conduit 36 which leads to the cuvette 14 (FIG. 1).

The vapor density is maintained by varying the flow rate and the variations in flow rate are obtained through the bypass valve 112 which exhausts air from the pump through a conduit 116 and the exhaust pipe 118. The bypass valve includes an electromagnetically-operated valve opening which varies in size in accordance with the signal received from the differential amplifier 114.

The differential amplifier is controlled by the signal on conductor 76 indicating the moisture in the inner cuvette chamber 40 (FIG. 2) and the setting of selector switch 115 which remains constant. The operator selects a fixed potential with the selector switch 115 at the start of operation in the illustrative system of FIG. 3. In the preferred embodiment an actual reading is selected by the operator and stored in memory.

This potential is maintained by the flow of dry air through the cuvette which is varied by the bypass valve 112 under the control of the differential amplifier 114 so that, as the moisture within the chamber varies, a variation is caused in the signal on conductor 76 which causes the output of the differential amplifier 114 to vary. This varies the flow rate of the dry air until the null point is again established within the cuvette and the moisture is maintained constant irrespective of the transpiration rate of the leaf being measured.

More specifically, as the moisture increases, the bypass valve 112 receives a signal from the differential amplifier 114 which causes it to close. This increases the rate of flow of dry air until the moisture returns to its previous level as indicated by the signal on conductor 76. If the moisture decreases below that level, the signal on conductor 76 causes the differential amplifier to send a signal to the bypass valve 112 to open the orifice more and reduce the rate of dry air flow as indicated by the flow meter 108, thus permitting more moist air in the chamber. In this manner, the moist air is maintained constant and the air flow changes.

The data conversion section 82 converts the input data to digital form and records the data in memory at operator-selected times to be used in the calculations of transpiration rate and diffusion resistance. The selection of digital form for the calculations is a result of the use of a microprocessor in the preferred embodiment, and analog form could be used in a manner known in the art.

The temporary storage of the information permits readout at intervals selected by the operator. Although periodic intervals are selected for readout by storing the data at those intervals, the instrument itself follows the transitory nature of the transpiration of the plant life. Thus, the transpiration rate of the plant varies dynamically with conditions and the instrument follows that change by measuring the moisture in the chamber and causing the flow of dry air to instantaneously follow such changes even though data is stored at periodic intervals for convenience in calculation and recording of the data.

To convert the data to digital form, the data conversion section 82 includes first, second and third analog-to-digital converters 122, 124 and 126, each being electrically connected to a respective one of the conductors 90, 74 and 72 to receive corresponding signals representing flow rate, temperature of the chamber and temperature at the surface of the leaf in analog form and to convert these signals to digital signals representing the corresponding values.

To permit the use of the values for calculations at preselected intervals of time, the data conversion section 82 includes first, second and third memories 128, 130 and 132, a hold switch 134 (controlled by the toggle actuator 28, FIG. 1). The first, second and third memories 128, 130 and 132 are each electrically connected to a corresponding one of the first, second and third analog-to-digital converters 122, 124 and 126 by a respective one of the conductors 138, 140 and 142.

Digital information is received by the first, second and third memories 128, 130 and 132 through conductors 138, 140 and 142 for recording when the hold switch 134 is in the hold position to apply a signal to the memories until it is moved to the release position. Thus, the toggle actuator 28 manually controls the hold switch 134 to provide a manually controlled means for recording the vapor density at a manually selected time and the same means controls a means for recording said rate of flow of air at the manually selected time by causing data to be recorded in the first, second and third memories 138, 130 and 132.

The calculation section 84 calculates the transpiration rate and the diffusion resistance from the signals that it receives from the data conversion section on conductors 92, 94 and 96 and the signal it receives from the display and leaf-size selection section 86 through conductor 102. The calculated information is transmitted to the display and leaf-size selection section 86 through conductors 98 and 100 as will be described hereinafter.

To calculate the transpiration rate, the calculator section 84 includes a vapor density memory 144, a multiplier 146 and a divider 148. The vapor density memory 144 is electrically connected to conductor 94 to receive a signal indicating the temperature in the chamber and to conductor 96 to receive a signal indicating the moisture in the chamber.

These two signals address the memory to a memory location in which the vapor density corresponding to the temperature and moisture is recorded. This value is read out of the vapor density memory into the multiplier 146 through a readout conductor.

The multiplier 146 is electrically connected to the vapor density memory 144, as mentioned above, well as to conductor 96 to receive a signal which indicates the flow rate of air through the cuvette, which is representative of the moisture in the chamber. These two signals are multiplied and the product applied to the divider 148.

The divider 148, besides receiving signals which indicate the product of the rate of flow of air and the vapor density as a dividend, receives a signal on conductor 102 as the divisor. The signal on conductor 102 (divisor) indicates the area of the leaf being examined which is controlled by the opening between the O-rings 56 and 58 (FIG. 2) which determines the amount of leaf being examined. The resulting quotient is equal to the transpiration rate and it is applied to the display and leaf-size selection section 86 through a conductor 98. The manual leaf-size selector signal is set at the factory to correspond to the size of the O-rings.

To measure the diffusion resistance, the calculator section 84 includes vapor density memory 150, a first divider 152, a subtract one circuit 154, a multiplier 156 and a second divider 158.

The vapor density memory 150 is electrically connected to the memory 132 through a conductor 92 which addresses a table within the memory for the vapor density at saturation of water corresponding to the temperature signal serving as the address. Conductor 92 contains information indicating the temperature of the leaf, which is assumed to be at saturation, so that the output of the vapor density memory 150 represents the water vapor density of the leaf.

The divider 152 has its dividend input electrically connected to the vapor density memory 150 and its divisor input electrically connected to the vapor density memory 144, which as described earlier, is addressed by conductors 94 and 96 to provide an output proportional to the vapor density of the chamber. The divider 152 divides the vapor density of the leaf by the vapor density in the chamber.

The subtract one circuit 154 subtracts one from the quotient signal provided by the divider 152 to which it is electrically connected and applies the difference to one input of the multiplier 156 to which it is electrically connected. The multiplier is also electrically connected to conductor 102 to receive the leaf-size information indicating the area. Those two inputs are multiplied together and applied to the dividend input of the divider 158, the divisor input of which is electrically connected to conductor 96 to divide by the flow rate, providing a quotient on conductor 100 which is equal to the diffusion resistance.

The display and leaf-size selection section 86 includes a flow rate meter 160, a transpiration rate readout 162, a manual aperture-area selector 164 and a diffusion resistance readout 166. The flow rate meter 160 is electrically connected to conductor 88 to indicate the flow rate of air through the inner cuvette chamber; the transpiration readout 162 is electrically connected to conductor 98 and provides a digital readout of the transpiration rate; and the diffusion resistance readout 166 is electrically connected to conductor 100 and provides a readout of the diffusion resistance.

The manual aperture-area selector 164 provides to conductor 102 a signal representing the area of the section of leaf being inspected. It is included because the cuvette 14 is adapted to have the lever 24 replaced so that different size apertures are available for leaves. Since the leaf area is a factor to be considered in the transpiration rate and diffusion resistance, a correction is applied for the size of the aperture and the manual leaf-size selector provides that correction factor.

Conductors 120A and 120B are connected to the range selector 111 which selects one of the two for application to the A/D converter. Conductor 120A is electrically connected to conductor 88 to provide a continuous indication on the meter within the display section 86 of flow rate.

The range selector 111 may be a switch which selects the output from the flow meter 108 which depends upon the rate of flow, selecting 120A when the rate of flow is below a predetermined point and 120B when it is above that point. This may be done by an operator watching the meter 160 and using a manual switch or it may be done automatically be range selectors, many of which are known in the art. In the preferred embodiment, the microprocessor does it as part of its program control through the use of a comparator technique which is also well known in the art.

Figures 4, 5:
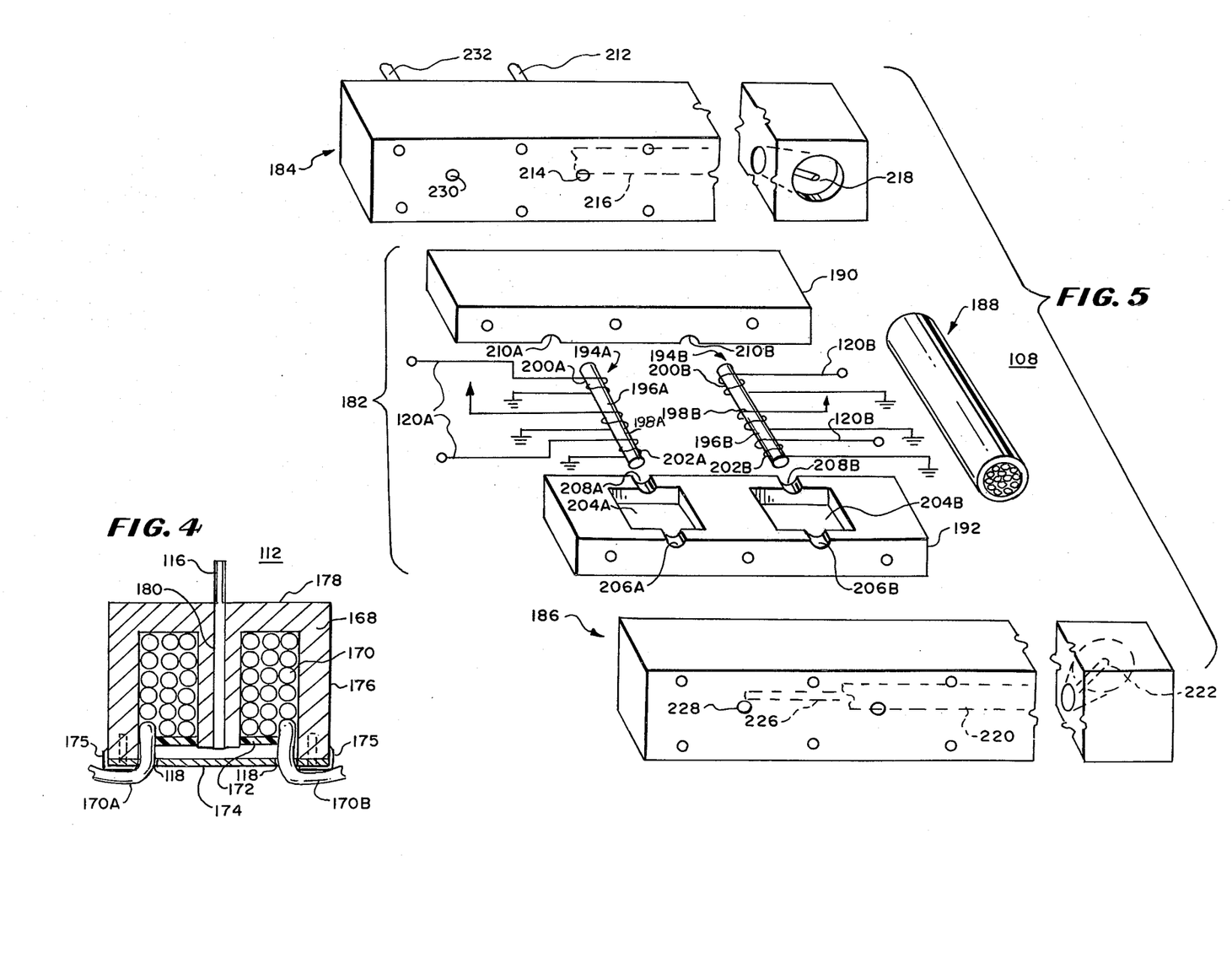
FIG. 4 is a simplified sectional view of a portion of the embodiment shown in FIG. 3.
FIG. 5 is a simplified, exploded, perspective view of a portion of the embodiment illustrated in FIG. 3.

In FIG. 4, there is shown a sectional view of the bypass valve 112 including a steel frame 168, a conductive winding 170, a plastic insulating spool 172, and a steel valve plate 174.

The steel frame 168 has a cylindrical outer wall 176 and a flat end 178 from which a steel center post 180 extends toward an open end which is closed by the plastic insulative spool 172 and the steel valve plate 174.

To provide a bypass flow path for dry air, the air conduit 116 from the pump 104 (FIG. 3) passes through the end 178 and the center post 180 of the steel frame and extends to a position just below the steel plate 174. The steel plate 174 is loosely held by a plastic retaining ring 175.

This construction is such that, when the steel plate 174 is spaced a short distance from the center post 180, air exhausts radially outwardly through slots such as those shown at 118 in the steel plate 174, thus reducing the flow rate to the inner cuvette chamber by way of the conduit 36 (FIGS. 1 and 2) and when the steel plate 174 is pressed against the center post 180 air is blocked from exhaust, thus increasing the flow rate to the inner cuvette chamber.

To control the position of the steel plate 174, windings 170 have one end 170A electrically connected to the output of the differential amplifier 114 (FIG. 3) and the other end electrically grounded so that the differential amplifier 114 sends current through the winding to set up a magnetic field varying in intensity with the variations in humidity.

To control the exhaust of air to the atmosphere, the magnetic field set up by the winding 170 extends through the center post 180 from the end 178 toward the metal plate 174, passing through the air gap to the metal plate and traversing radially to the side walls 176, and from there back to the end plate 178 to complete the magnetic path. When the field is strong, the plate is pulled downwardly to block the exhaust of air and when it is weak it moves upwardly to reduce the restriction to air. Consequently, current from the differential amplifier 114 controls the rate of flow of air through the conduit 36 to the inner cuvette (FIG. 3).

The steel valve plate 174 may be one or two thin strips of metal or a disc selected for suitable flexibility. It may be held in place by a plastic retaining cap, screws, adhesive tape or any other suitable means. Moreover, instead of a magnetic field spacing the valve member, other alternatives may be used such as piesoelectric, thermal, or servo valves may be used.

In FIG. 5, there is shown an exploded perspective view of the flow meter 108 having a flow rate sensing unit 182, first and second manifolds 184 and 186 and a bypass 188.

The flow rate sensing unit 182 includes a top compartment 190, a bottom compartment 192, a first flow rate sensing unit 194A and a second flow rate sensing unit 194B. The flow rate sensing units 194A and 194B each include a corresponding one of the air flow tubes 196A and 196B, heaters 198A and 198B, first temperature sensors 200A and 200B and second temperature sensors 202A and 202B.

The bottom and top housings 190 and 192 include two open compartments shown at 204A and 204B in the bottom section of 192. On each side of each of the compartments are cutaway portions shown at 206A and 206B on one side of the bottom portion 192 and at 208A and 208B on the other side of the bottom portion 192. Corresponding cylindrical openings are cut in the top portion 190, two of which are shown at 210A and 210B.

When assembled, the tubes 196A and 196B are held between the two housing halves 190 and 192 with their ends resting in the grooves 206, 208, 210 and the unnumbered grooves on both sides of the two compartments 204A and 204B.

The heaters 198A and 198B are centered within the compartments 204A and 204B with the temperature sensing devices 200A, 200B, 202A and 202B being positioned within the compartments near the ends where they sense the differences in temperature between the ends of each tube caused by the flow of air through the tubes in a manner known in the art. The conductors 120A and 120B provide a potential that is proportional to the difference in temperature and therefore the flow rate through the tubes.

To provide the flow of air to the flow rate sensing unit 182, the manifold block 184 receives a conduit 212 which communicates with the manual flow rate adjustment 106 (FIG. 3) to receive air from the pump and permits its passage through a passageway 214 in the manifold block 184.

To provide a parallel path for air through measuring tube 194B and bypass cylinder 188, the passageway 214 is connected to one end of the tube 194B and to a conduit 216 within the manifold block 184 which communicates with a large cylindrical opening 218 that is sealed except where it is adapted to receive one end of the bypass cylinder 188. The other end of the tube 194B fits within a similar opening in the block 186, which opening does not pass through the block but passes laterally in a first direction through a conduit 220 into an opening 222 in the manifold 186 sized to receive the other end of the bypass cylinder 188 and through another lateral conduit 226 to an opening which communicates with one end of the tube 194A.

To cause all of the air to pass through measuring tube 194A before leaving the flow meter 108, the other end of the tube 194A passes through an opening in the manifold 184 parallel to the opening 230 and communicates with a conduit 232. The conduit 232 is connected to one end of the desiccant 110 (FIG. 3) to permit the air to continue on to the conduit 36 after its flow rate has been measured.

The bypass cylinder 188 includes 39 tubes within its center, each having the same diameter as the tubes 194A and 194B. Its two ends fit within different ones of the manifolds 184 and 186 in the openings 218 and 222 so that it is sealed at both ends except for the lateral opening 216 in the manifold 184 at one end and the opening 220 in the manifold 186 at its other end.

Tubes 194A and 194B as well as the 39 tubes in the bypass cylinder 188 are each one and one-half inches long. They have an inner diameter of 0.047 and an outer diameter of 0.058 inches. The inner diameter of the bypass cylinder 188 is 0.4 and its ouer diameter is 0.440.

The tubes 194A, 194B, and the 39 tubes in the bypass cylinder 188 are of such a size as to provide laminar flow rather than turbulent flow through their lengths. The laminar flow permits the flow rate to be accurately meassured in the tubes 194A and 194B and causes the flow rate in the tube 194B, which is parallel to the bypass cylinder 188, to be linear with the flow in the identical tubes within the bypass cylinder 188.

In operation when fully assembled, air from the pump after flowing through the manual flow rate adjustment passes into the conduit 212 and from there into the opening 214 within the manifold 184. A portion of the air passes through the conduit 216 and through the bypass cylinder 188 and another portion passes through the tube 194B in parallel in the ratio of 1:40 since the conduits 216 and 220 which communicate with the opposite ends of the bypass cylinder 188 are much larger than the entrances into the manifolds 184 aand 186, being approximately 30 times the same size to permit this parallel flow.

All of the air passing from the conduit 212 through the tubes into the manifold 186 passes through the conduit 226 into the conduit 228 and from there through the tube 194A. From the tube 194A it passes through the conduit 230 and out the conduit 232 through the desiccant container 110 and the conduit 36 to the inner cuvette (FIGS. 1, 2 and 3).

This flow of air is measured in two places and provides a signal on conductors 120A and 120B, with the signal on 120A indicating the total flow of air and the signal on 120B indicating one-fortieth of the flow of air. During low flow rates, the range selector 111 (FIG. 3) (or the microprocessor in the preferred embodiment) selects the signal on 120A to represent the flow rate and during higher flow rates selects the signal on conductor 120B which contains a built-in range ratio of approximately 1:40 so as to provide a more precise measurement. The exact ratio is measured at the factory for calibration. This selection may be manual by viewing the flow meter 160 or automatic under the control of the signal from the flow meter 108 through a level detector as known in the art.

The flow rate is measured by the temperature differential caused as the air flows through the tubes 194A and 194B. Heat is moved in the direction of flow in a manner proportional to the flow and the potential difference at the thermocouples therefore indicates the rate of flow in a manner known in the art.

Figure 6:
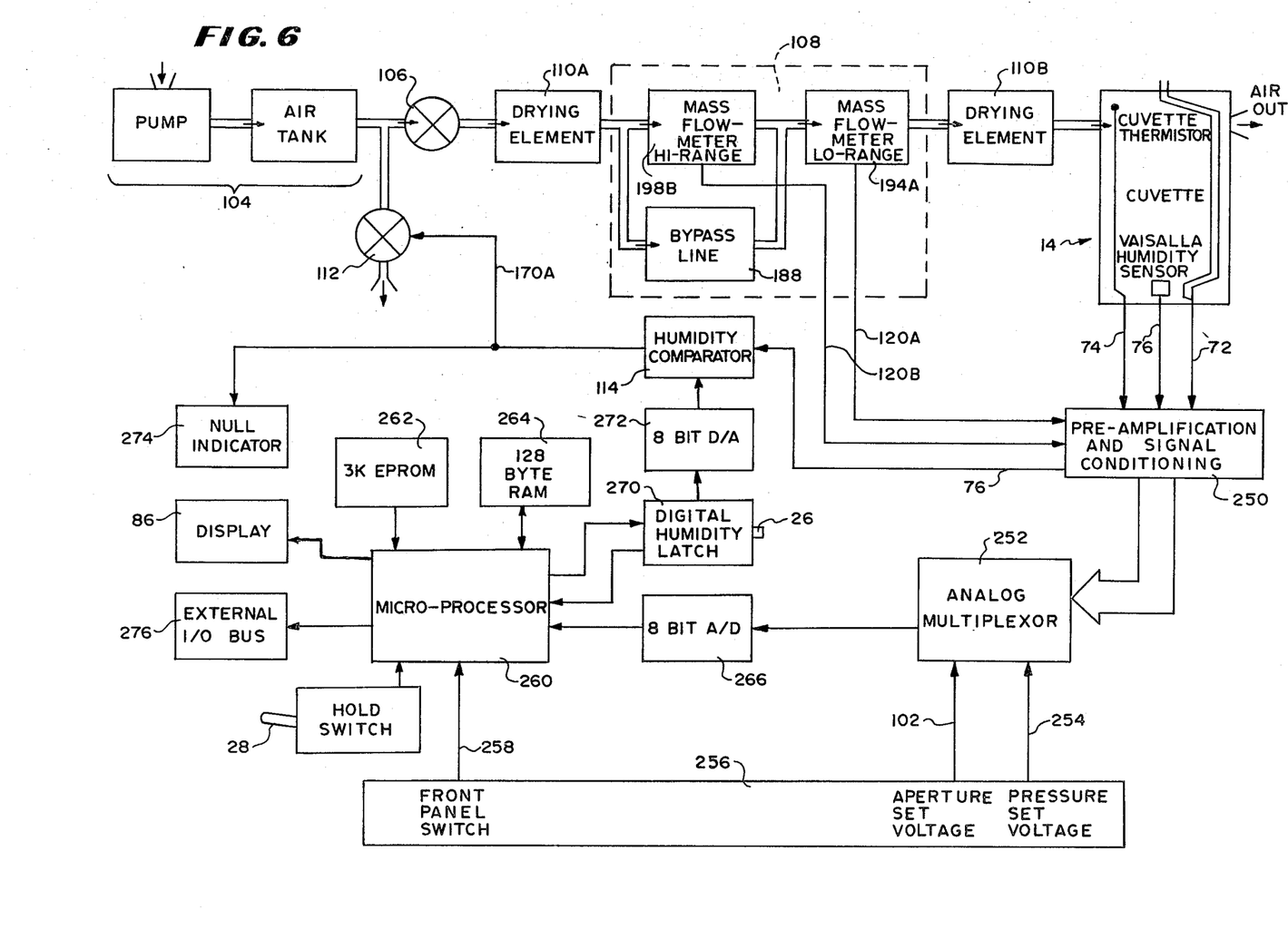
FIG. 6 is a block diagram of the system as used in the preferred embodiment.

In FIG. 6, there is shown a block diagram of the preferred embodiment showing the pump 104 which includes a pumphead and an airtank, the manually adjustable valve 106, a first desiccant tube 110A, a flow meter 108, a second desiccant tube 110B and the cuvette 14 as described above.

The preamplification and signal conditioning section shown generally at 250 receives the flow rate signals on conductors 120A and 120B and the leaf temperature, cuvette temperature and humidity readings on conductors 72, 74 and 76 respectively. These signals are amplified as necessary and transmitted to an analog multiplexor 252.

Certain voltages are provided through a conventional set of switches and dividers indicated generally at 256 to the analog multiplexor 252 and a microprocessor 260.

The analog multiplexor 252 also receives an aperture-set signal through conductor 102 and a pressure-set signal on a conductor 254 which corrects the flow rate indication. The correction is an altitude correction which changes the flow rate of air measurement from a mass flow rate to a volumetric flow rate. The mass flow rate is measured by the flow meter used in the preferred embodiment whereas the equations for computation require a volume flow-rate figure.

The switching circuit 256 includes a selector switch which selects the data to be read out, illustrated by a conductor 258 communicating with the microprocessor indicated at 260. This microprocessor 260 is the aforementioned RCA 1802 microprocessor.

The microprocessor 260 receives signals from the hold switch controlled by the toggle actuator 28 and communicates with external memories 262 and 264 which perform the functions of the memory elements as described generally above. Data is applied by the analog multiplexor 252 to an analog-to-digital converter 266 which applies the data in digital form to the microprocessor 260. This performs the function shown by the separate analog-to-digital converters in the explanation associated with FIG. 3.

To provide a null voltage such as that served by the switch 115 in the circuit of FIG. 3, the microprocessor applies continuous digital indications of the humidity to a digital humidity latch 270. The operator causes the latch 270 to record this reading at any time by depressing the push-button actuator 26. The recorded value of humidity is then converted to an analog value in the digital-to-analog converter 272 connected to the latch 270.

The output from the digital-to-analog converter 272 is applied to the differential amplifier indicated at 114 as a comparator.

The comparator 114 receives the humidity signal on conductor 76 after being processed by the preamplification and signal conditioning section 250 for comparison and control of a null indicator 274 and for control of the bypass valve 112 in the manner described in connection with FIG. 3. The null indicator is a light on the console 16 (FIG. 1). Data from the latch 270 is also fed back to the microprocessor at 260 for use in calculations explained in connection with FIG. 3. To connect the data output to printers and the like, a conventional external input-output bus 276 in FIG. 6 is provided.

From the above description, it can be understood that the porometer and the method of stomatal measurements of this invention have several advantages, such as: (1) the measurements of stomatal resistance are relatively precise since they are based on measurements that provide the vapor density of the leaf and of the chamber separately rather than just the vapor density of the chamber; (2) the temperature measurements of the leaf are made with accuracy because of the small size of the thermocouple used for the measurements; (3) the flow rate measurements are taken over an unusually wide dynamic range with precision; (4) the flow rate automatically adjusts to maintain the moisture in the cuvette constant; and (5) the flow meter is linear over a wide dynamic range.

Although a preferred embodiment of the invention has been described with some particularity, many modifications and variations may be made in the preferred embodiment without deviating from the invention in the light of the above teachings. Therefore, it is to be understood that, within the scope of the appended claims, the invention may be practiced other than an specifically described.

What is claimed is:

1. A method of determining characteristics of a plant related to its ability to create humidity in its vicinity comprising the steps of:
    measuring the humidity created by the plant in a location;
    forcing dry gas through said location;
    automatically changing the rate of flow of said dry gas in response to changes in the measured humidity created by the plant to maintain the humidity constant;
    measuring the rate of flow of the dry gas for maintaining the humidity constant;
    measuring the vapor density; and
    calculating the characteristics of the plant from said measurements.

2. A method of determining characteristics of plants comprising the steps of:
    measuring the humidity created by the plant in a location;
    automatically forcing sufficient dry gas through said location to maintain the humidity constant;
    measuring the rate of flow of the dry gas for maintaining the humidity constant;
    measuring the vapor density;
    calculating the characteristics of the plant from said measurements; and
    the step of calculating the characteristics of the plant including the steps of: measuring the vapor density and rate of flow of dry gas at least at a first time and calculating said characteristics at a second time based on said measurements at said first time whereby the calculated characteristics are independent of the rate of flow of gas and the vapor density at the second time.

3. A method according to claim 2 in which the step of measuring vapor density includes the steps of measuring the vapor density of the plant and measuring the vapor density of the area in a chamber adjacent to the plant.

4. A method according to claim 3 in which the step of measuring the vapor density of the plant includes the step of sensing the temperature adjacent to the plant with a small temperature sensor.

5. A method according to claim 4 in which the step of measuring the temperature of the plant includes the step of measuring the temperature of the plant with a small thermocouple pressed against the surface of the plant.

6. A method according to claim 5 in which the step of automatically forcing sufficient dry gas through said location includes the steps of:
    forcing gas into the chamber;
    removing dry gas from said chamber; and
    controlling the flow of dry gas through an automatically controlled magnetic bypass valve controlled by the moisture in said chamber.

7. A method according to claim 6 in which the step of measuring the rate of flow of gas includes the step of forcing said dry gas through laminar flow paths and measuring the rate of flow in said laminar flow paths.

8. A method according to claim 7 in which the step of measuring the flow rate of gas includes the steps of:
    forcing the gas through a plurality of paths;
    selectively measuring the rate of flow of dry gas in a first of said plurality of paths and a second of said plurality of paths;
    the step of measuring the flow rate of gas in a second path including the step of measuring it in a second path that is in series with said first path and in parallel with a plurality of still other of said plurality of paths; and
    said step of forcing the gas through a plurality of paths including the step of forcing the gas through a plurality of paths with laminar flow.

9. A method of determining characteristics of plants comprising the steps of:
    measuring the humidity created by the plant in a location;
    automatically forcing sufficient dry gas through said location to maintain the humidity constant;
    measuring the rate of flow of the dry gas for maintaining the humidity constant;
    measuring the vapor density;
    calculating the characteristics of the plant from said measurements; and
    the step of measuring vapor density including the steps of measuring the vapor density of the plant and measuring the vapor density of the area in a chamber adjacent to the plant.

10. A method according to claim 9 in which the step of measuring the vapor density of the plant includes the step of sensing the temperature adjacent to the plant with a small temperature sensor.

11. A method according to claim 10 in which the step of measuring the temperature of the plant includes the step of measuring the temperature of the plant with a narrow thermocouple pressed against the surface of the plant.

12. A method according to claim 11 in which the step of automatically forcing sufficient dry gas through said location includes the steps of:
forcing gas into the chamber;
removing dry gas from said chamber; and
controlling the flow of dry gas through an automatically controlled magnetic bypass valve controlled by the moisture in said chamber.

13. A method according to claim 12 in which the step of measuring the rate of flow of gas includes the step of forcing said dry gas through laminar flow paths and measuring the rate of flow in said laminar flow paths.

14. A method according to claim 13 in which the step of measuring the flow rate of gas includes the steps of:
forcing the gas through a plurality of paths;
selectively measuring the rate of flow of dry gas in a first of said plurality of paths and a second of said plurality of paths;
the step of measuring the flow rate of gas in a second path including the step of measuring it in a second path that is in series with said first path and in parallel with a plurality of still other of said plurality of paths; and
said step of forcing the gas through a plurality of paths including the step of forcing the gas through a plurality of paths with laminar flow.

15. A method of determining characteristics of plants comprising the steps of:
measuring the humidity created by the plant in a location;
automatically forcing sufficient dry gas through said location to maintain the humidity constant;
measuring the rate of flow of the dry gas for maintaining the humidity constant;
measuring the vapor density;
calculating the characteristics of the plant from said measurements; and
the step of automatically forcing sufficient dry gas through said location including the steps of: forcing gas into the chamber; removing dry gas from said chamber; and controlling the flow of dry gas through an automatically controlled magnetic bypass valve controlled by the moisture in said chamber.

16. A method according to claim 15 in which the step of measuring the rate of flow of gas includes the step of forcing said dry gas through laminar flow paths and measuring the rate of flow in said laminar flow paths.

17. A method according to claim 16 in which the step of measuring the flow rate of gas includes the steps of:
forcing the gas through a plurality of paths;
selectively measuring the rate of flow of dry gas in a first of said plurality of paths and a second of said plurality of paths;
the step of measuring the flow rate of gas in a second path including the step of measuring it in a second path that is in series with said first path and in parallel with a plurality of still other of said plurality of paths; and
said step of forcing the gas through a plurality of paths including the step of forcing the gas through a plurality of paths with laminar flow.

18. A method of determining characteristics of plants comprising the steps of:
measuring the humidity created by the plant in a location;
automatically forcing sufficient dry gas through said location to maintain the humidity constant;
measuring the rate of flow of the dry gas for maintaining the humidity constant;
measuring the vapor density;
calculating the characterisitics of the plant from said measurements; and
the step of measuring the rate of flow of gas includes the step of forcing said dry gas through laminar flow paths and measuring the rate of flow in said laminar flow paths.

19. A method according to claim 18 in which the step of measuring the flow rate of gas includes the steps of:
forcing the gas through a plurality of paths;
selectively measuring the rate of flow of dry gas in a first of said plurality of paths and a second of said plurality of paths;
the step of measuring the flow rate of gas in a second path including the step of measuring it in a second path that is in series with said first path and in parallel with a plurality of still other of said plurality of paths; and
said step of forcing the gas through a plurality of paths including the step of forcing the gas through a plurality of paths with laminar flow.

20. A porometer comprising:
cuvette means for mounting a portion of a plant in communication with the interior of said cuvette;
means for measuring humidity in the cuvette means;
means for measuring vapor density;
means for forcing a dry gas through the cuvette means;
means for measuring the rate of flow of dry gas through the cuvette means; and
means for automatically controlling the rate of flow of dry gas through the cuvette means so as to maintain the humidity within the cuvette means constant.

21. A porometer according to claim 20 in which the means for measuring vapor density includes a manually controlled means for recording said vapor density at a manually selected time.

22. A porometer according to claim 21 in which said manually controlled means includes means for recording said rate of flow of air at said manually selected time.

23. A porometer according to claim 22 in which said means for measuring vapor density includes a means for measuring the vapor density of the plant and the vapor density within the cuvette means.

24. A porometer according to claim 23 in which the means for measuring the vapor density of the plant includes a small wire temperature sensor adapted to be pressed against the plant.

25. A porometer according to claim 24 in which the small temperature sensor is a one-mil thermocouple spring.

26. A porometer according to claim 25 in which said means for automatically controlling the rate of flow of gas includes a conduit communicating with said source of gas and a means for changing an exhaust port in said conduit in proportion to a signal related to the change in said measured humidity.

27. A porometer according to claim 26 in which said means for controlling the rate of flow of gas further includes:
a means for comparing the measured humidity with a standard humidity and deriving a third signal; and
said third signal being applied to a means for changing the size of an exhaust port in proportion to said third signal.

28. A porometer according to claim 27 in which said means for measuring said rate of flow of gas includes a means for measuring the rate of flow of gas through a laminar path.

29. A porometer according to claim 28 in which said means for measuring includes:
a first laminar flow path;
second and third laminar flow paths;
said second and third laminar flow paths being in parallel;
said first flow path being in series with said parallel combination of second and third flow paths;
means for measuring the rate of flow through said first flow path; and means for measuring the rate of flow through said second flow path.

30. A porometer according to claim 29 in which:
said first and second flow paths are narrow diameter tubes of equal length and internal diameter; and
said third flow path includes a plurality of tubes in parallel with said first and second tubes.

31. A porometer according to claim 20 in which said means for measuring vapor density includes a means for measuring the vapor density of the plant and the vapor density within the cuvette means.

32. A porometer according to claim 31 in which the means for measuring the vapor density of the plant includes a small wire temperature sensor adapted to be pressed against the plant.

33. A porometer according to claim 32 in which the small temperature sensor is a one-mil thermocouple spring.

34. A porometer according to claim 33 in which said means for automatically controlling the flow of gas includes a conduit communicating with said source of gas and a means for changing an exhaust port in said conduit in proportion to a signal related to the change in said measured humidity.

35. A porometer according to claim 34 in which said means for controlling the flow of gas further includes:
means for comparing the measured humidity with a standard humidity and deriving a third signal; and
said third signal being applied to a means for changing the size of an exhaust port in proportion to said third signal.

36. A porometer according to claim 35 in which said means for measuring said rate of flow of gas includes a means for measuring the rate of flow of gas through a laminar path.

37. A porometer according to claim 36 in which said means for measuring includes:
a first laminar flow path;
second and third laminar flow paths;
said second and third laminar flow paths being in parallel;
said first flow path being in series with said parallel combination of second and third flow paths;
means for measuring the rate of flow through said first flow path; and
means for measuring the rate of flow through said second flow path.

38. A porometer according to claim 37 in which:
said first and second flow paths are narrow diameter tubes of equal length and internal diameter; and
said third flow path includes a plurality of tubes in parallel with said first and second tubes.

39. A porometer according to claim 20 in which said means for automatically controlling the flow of gas includes a conduit communicating with said source of gas and a means for changing an exhaust port in said conduit in proportion to a signal related to the change in said measured humidity.

40. A porometer according to claim 39 in which said means for controlling the flow of gas further includes:
means for comparing the measured humidity with a standard humidity and deriving a third signal; and
said third signal being applied to a means for changing the size of an exhaust port in proportion to said third signal.

41. A porometer according to claim 40 in which said means for measuring said rate of flow of gas includes a means for measuring the rate of flow of gas through a laminar path.

42. A porometer according to claim 41 in which said means for measuring includes:
a first laminar flow path;
second and third laminar flow paths;
said second and third laminar flow paths being in parallel;
said first flow path being in series with said parallel combination of second and third flow paths;
means for measuring the rate of flow through said first flow path; and
means for measuring the rate of flow through said second flow path.

43. A porometer according to claim 42 in which:
said first and second flow paths are narrow diameter tubes of equal length and internal diameter; and
said third flow path includes a plurality of tubes in parallel with said first and second tubes.

44. A porometer according to claim 20 in which said means for measuring said rate of flow of gas includes a means for measuring the rate of flow of gas through a laminar path.

45. A porometer according to claim 44 in which said means for measuring includes:
a first laminar flow path;
second and third laminar flow paths;
said second and third laminar flow paths being in parallel;
said first flow path being in series with said parallel combination of second and third flow paths;
means for measuring the rate of flow through said first flow path; and
means for measuring the rate of flow through said second flow path.

46. A porometer according to claim 45 in which:
said first and second flow paths are narrow diameter tubes of equal length and internal diameter; and
said third flow path includes a plurality of tubes in parallel with said first and second tubes.

* * * * *

UNITED STATES PATENT AND TRADEMARK OFFICE
CERTIFICATE OF CORRECTION

PATENT NO. : 4,312,218

DATED : January 26, 1982

INVENTOR(S) : Robert D. Eckles

It is certified that error appears in the above—identified patent and that said Letters Patent is hereby corrected as shown below:

Column 3, line 6, change "stead-state" to --steady-state--;

Column 3, line 12, change "leaf:" to --leaf;--;

Column 3, line 25, change "the thermocouple" to --The thermocouple--;

Column 3, line 39, after "tables", add --.--;

Column 3, line 59, change "R= ($C_e/C_a$-1)A/F  Equation 1:" to --Equation 1:  R= ($C_e/C_a$-1)A/F--;

Column 3, line 61, change T= $FC_a$/A  Equation 2:" to --Equation 2:  T= $FC_a$/A--;

UNITED STATES PATENT AND TRADEMARK OFFICE
CERTIFICATE OF CORRECTION

PATENT NO. : 4,312,218
DATED : January 26, 1982
INVENTOR(S) : Robert D. Eckles

It is certified that error appears in the above—identified patent and that said Letters Patent is hereby corrected as shown below:

Column 8, line 52, change "divider" to --divisor--;

Column 11, line 50, change "ouer" to --outer--;

Column 11, line 68, change "aand" to --and--;

Column 13, line 47, change "an" to --as--.

Signed and Sealed this

First Day of June 1982

[SEAL]

Attest:

Attesting Officer

GERALD J. MOSSINGHOFF
Commissioner of Patents and Trademarks